United States Patent [19]
Coble et al.

[11] Patent Number: 5,002,539
[45] Date of Patent: Mar. 26, 1991

[54] IV RATE METER

[76] Inventors: Stephen J. Coble, 11001 Leolang Ave.; Edward J. Arkans, 8835 Mulberry Dr., both of Sunland, Calif. 91040

[21] Appl. No.: 36,029

[22] Filed: Apr. 8, 1987

[51] Int. Cl.⁵ .......................................... A61M 5/165
[52] U.S. Cl. .................................. 604/253; 73/861.41
[58] Field of Search .................................. 604/65-67, 604/245, 246, 251, 253; 73/861.41

[56] References Cited

U.S. PATENT DOCUMENTS

| | | | |
|---|---|---|---|
| 4,038,981 | 8/1977 | LeFevre et al. | 604/65 |
| 4,346,606 | 8/1982 | Cannon et al. | 604/253 |
| 4,397,648 | 8/1983 | Knute | 604/253 |
| 4,509,943 | 4/1985 | Hanzawa | 604/67 |
| 4,533,350 | 8/1985 | Danby et al. | 604/253 |
| 4,623,331 | 11/1986 | Cewers et al. | 604/65 |
| 4,668,216 | 5/1987 | Martin et al. | 604/253 |
| 4,681,569 | 7/1987 | Coble et al. | 604/253 |

Primary Examiner—Stephen C. Pellegrino
Assistant Examiner—Ralph A. Lewis
Attorney, Agent, or Firm—Head & Johnson

[57] ABSTRACT

A rate meter for use with an IV fluid administration system having a vertical transparent drip chamber, the rate meter having an elongated housing having a notch therein for receiving the drip chamber, and a spring bias moveable portion which engages the drip chamber so that the housing is held to the drip chamber in a horizontal manner, the housing having two light emitters positioned on one side of the drip chamber and a photodetector on the other side, the light path between the light emitters and the photodetector being affected by passages of drops of fluid through the drip chamber, circuitry for computing a volumetric flow rate based on the frequency of detected drops, an indicator for displaying the detected flow rate and a self-contained battery. The two light emitters are arranged to provide equal light intensity on the photodetector. The rate meter is further identified by the provision of an occluder element forming a part of the housing slideable portion which moves to intercept the light beam from one of the light emitters when the housing is removed from engagement with a drip chamber to provide an OFF signal employed by program instructions to de-energize most of the circuit components to thereby prolong battery life.

5 Claims, 4 Drawing Sheets

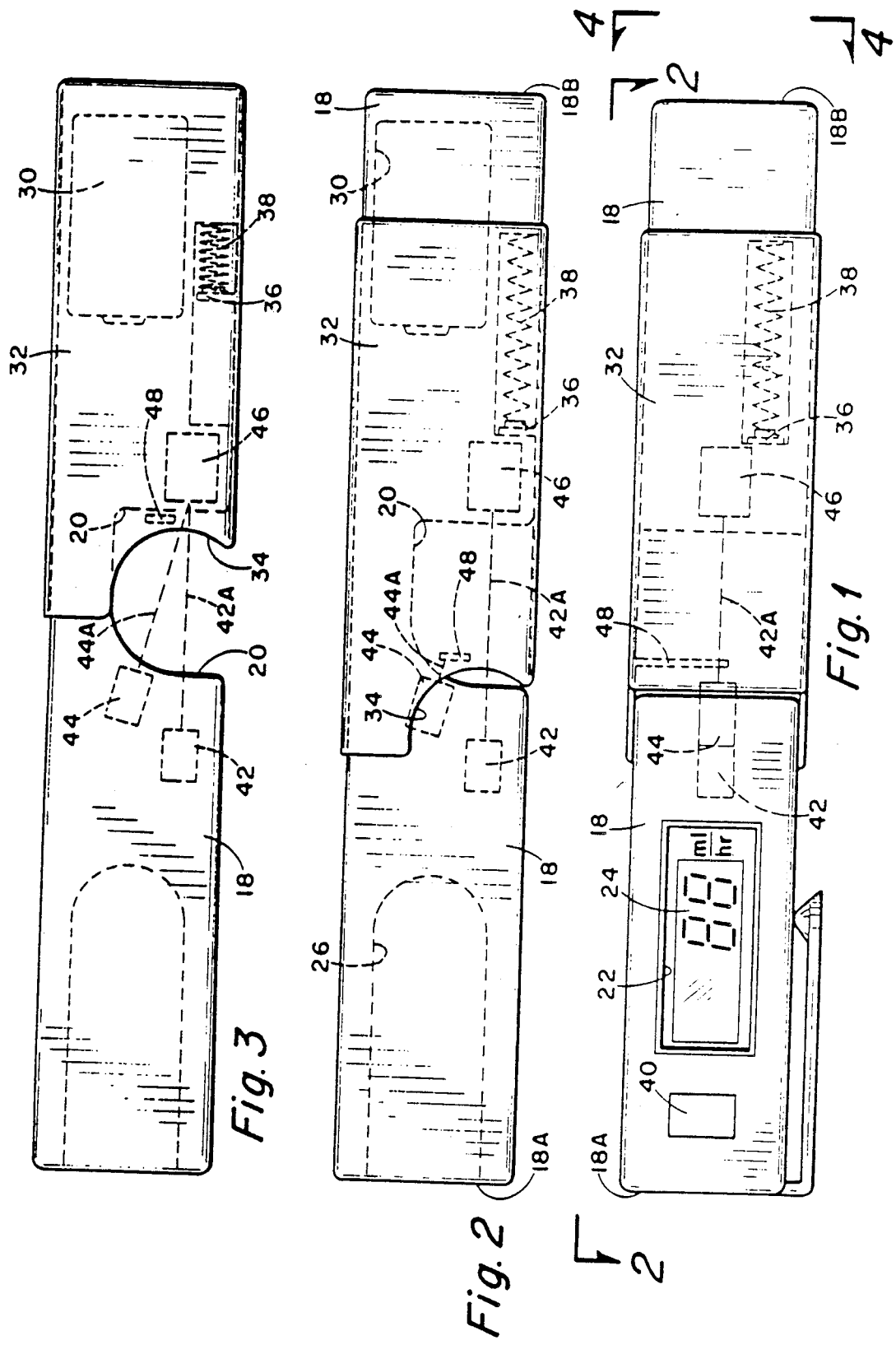

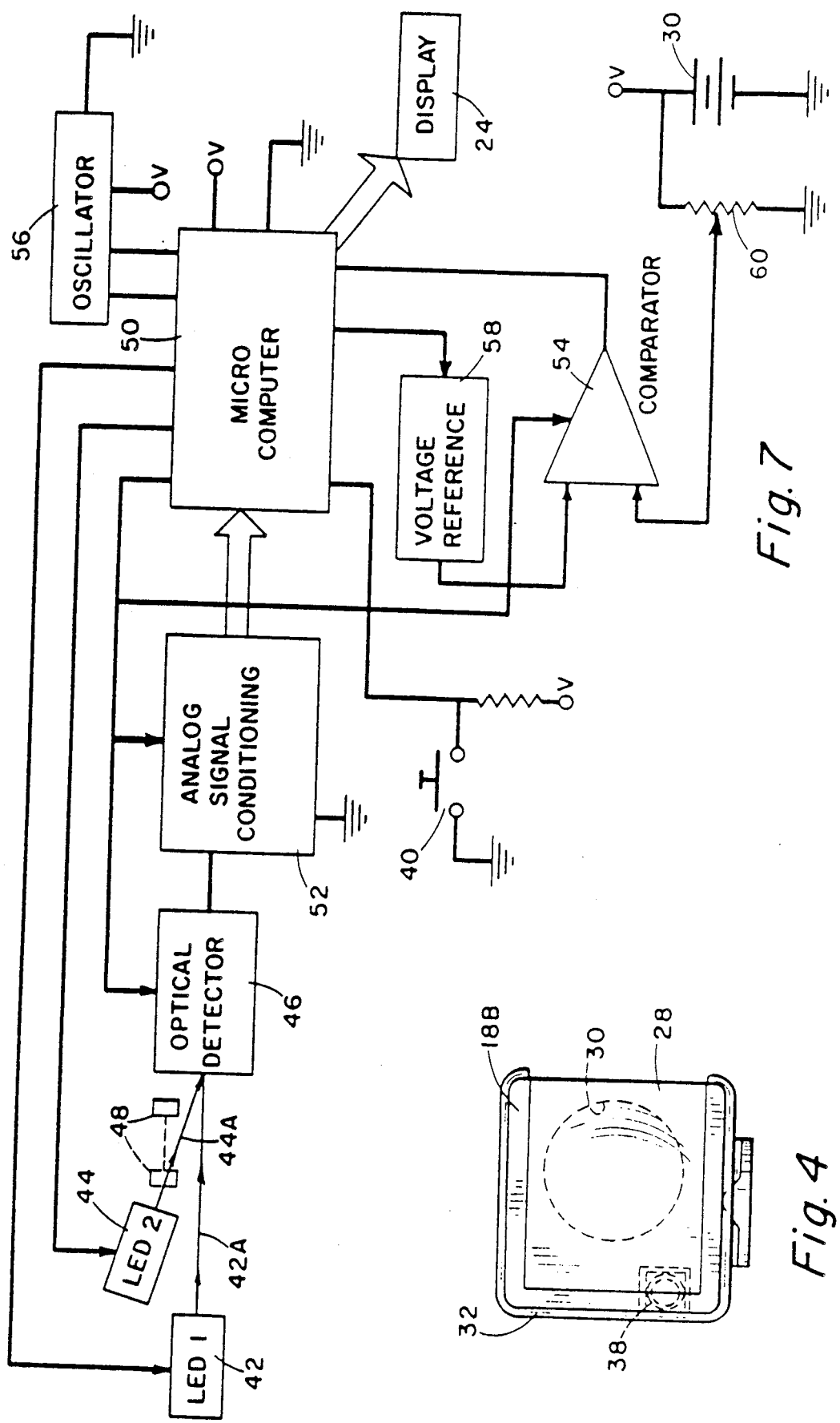

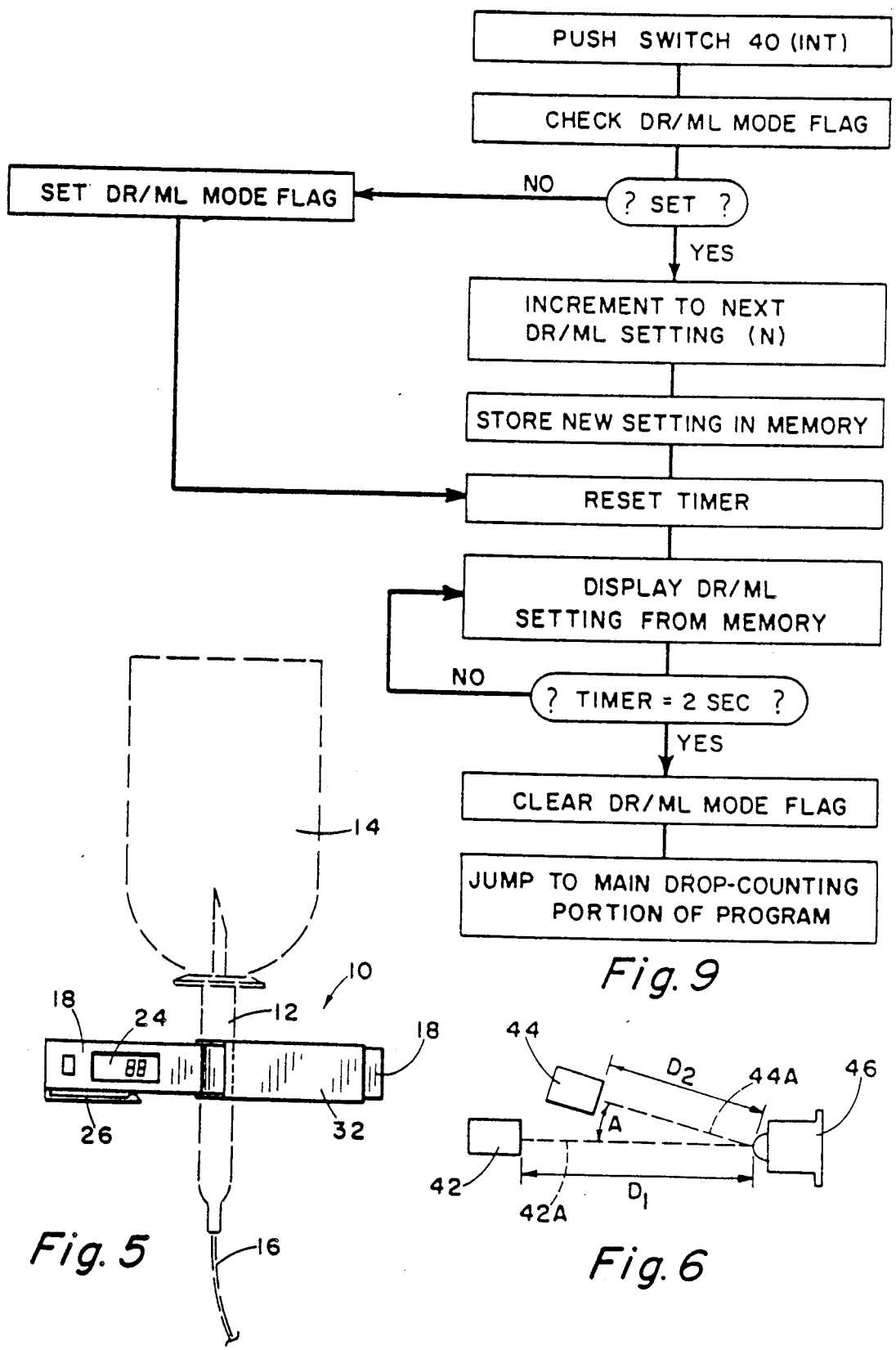

IV RATE METER

SUMMARY OF THE INVENTION

A common practice in hospitals is to inject fluid intravenously into patients at a relatively slow rate and over a relatively long period of time. It is important to know the rate of fluid flow into the patient when attempting to control the application of nutritive or medicinal components. The most usual means of intravenous (IV) fluid infusion employs a container, either a bottle or bag of fluid, which has attached to it a cylindrical transparent drip chamber. Within the chamber fluid drips from the container one drop at a time, that is, in drops, not in the form of a stream. The flow rate is controlled by controlling the drop rate. This is usually accomplished in one of two ways. In one way the hospital attendant regulates the flow manually by adjusting a roller clamp or other flow restricting devices while determining the drop rate (and thus the flow rate) visually. In the other way an electro-mechanical device automatically controls the rate by monitoring the drop rate and mechanically adjust a flow restriction element or the speed of a pump mechanism. In either the automatic or manual case described above, the flow rate is commonly determined by measuring the drop rate frequency and converting it to volume flow rate since the drop size for each IV set is known and is usually stated by the manufacture on the IV set labeling.

Several methods are used for automatically detecting passage of drops through a drip chamber. One of the most popular methods involves optical devices. Light emitters and photodetectors are placed on opposite sides of the drop's path. As the drops fall the light from the emitters is altered and is converted by the photodetector to an electrical signal. This signal is treated in an electrical circuit to determine if the alteration in the light path was, in fact, due to the presence of a drop or some artifact. Either a single light emitter and single photodetector can be employed or multiple light emitters or multiple detectors. Typically, systems use a plurality of light emitters and one photodetector or vice versa.

Others have provided concepts for achieving a rate meter for use in connection with IV fluid dispensation and for background information reference may be held to the following U.S. Pat Nos.: 4,397,648; 3,596,515; 4,469,480; 4,181,130; 4,038,982; 4,346,606; 3,553,583; 3,449,952; 3,545,271 and Des 269,998.

The rate meter of this invention is unique in several features, including its high degree of portability. In the preferred embodiment of the invention it is similar in overall configuration to a large fountain pen and is therefore easily carried in the shirt or coat pocket of a hospital attendant The rate meter of this invention is self-contained; that is, it does not have to be wired to any other energy source, instrumentation, or display. The rate meter is characterized by the ease with which it can be placed onto or removed from a drip chamber, its ability to adapt to various diameters of drip chambers, the ease of setting the instrument for various drip sizes, the automatic power down features which eliminate the requirement of an ON-OFF switch, and a circuit and computer program design which minimizes battery consumption by controlling the flow of battery current to the major circuit components through a microcomputer.

DESCRIPTION OF THE DRAWING

FIG. 1 is a front elevational view of an apparatus which employs the principal of the invention. The IV rate meter is shown in the non-use condition, that is, in the condition in which it is carried in the pocket of a hospital attendant.

FIG. 2 is a top view of the rate meter of FIG. 1 as taken along the lines 2—2 of FIG. 1.

FIG. 3 is a top view as in FIG. 2 but showing the housing moveable portion slid to the open position so that the rate meter can be attached to a drip chamber.

FIG. 4 is an end view taken along the line 4—4 of FIG. 1.

FIG. 5 is an elevational view showing the rate meter positioned on a drip chamber attached to an IV container showing the method in which the invention is employed to provide a read-out of the fluid flow rate of IV fluid being dispensed from the container.

FIG. 6 is a diagrammatic view of the arrangement of the light emitters and the photodetector employed in the rate meter for detecting the passage of a drop of fluid passing through the drip chamber.

FIG. 7 is a block diagram of the circuit employed in the rate meter.

FIG. 9 is a flow chart of a portion of the computer program showing the drop size setting routine, that is, the routine which establishes an input to the program of the drops per milliliter according to the fluid administration system with which the rate meter is being employed.

DETAILED DESCRIPTION OF THE PREFERRED EMBODIMENT

Figure 8:
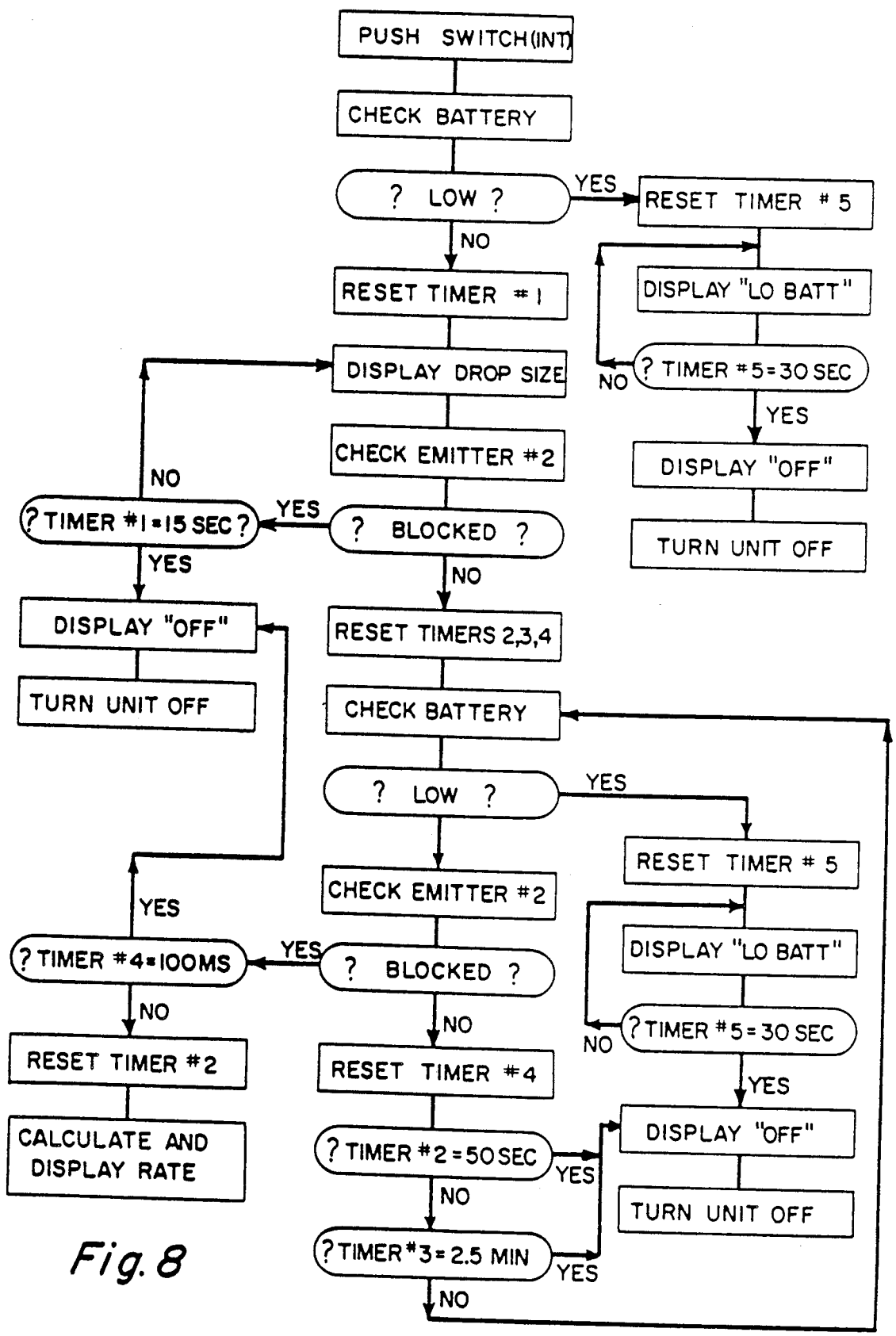
FIG. 8 is a flow chart of a portion of the computer program as employed in the rate meter illustrating the automatic OFF features of the program.

Referring now to the drawings and first to FIGS. 1 through 5 a preferred embodiment of the invention is illustrated. The rate meter of this invention is for use with an intravenous fluid administration system such as illustrated in FIG. 5. The rate meter is generally indicated by the numeral 10 and is shown affixed to a cylindrical, transparent drip chamber 12 which is attached to or formed as a part of an intravenous solution container 14. Fluid flows from container 14 as a sequence of drops passing vertically downwardly through the transparent drip chamber 12 and by tube 16 to intravenous injection into a patient. The rate of flow of fluid is determined by two factors, that is, the number of drops per minute, and the volumetric size of each drop Manufacturers of intravenous administration systems produce equipment having varying drop sizes according to the nature of construction of the equipment. The drop size characteristic of each piece of equipment is furnished by the manufacturer, and frequently is printed on labels affixed to the apparatus.

A unique aspect of the invention is that the rate meter 10 is of compact configuration, and can be approximately the size of a large fountain pen to be easily transported by hospital personnel in a shirt or coat pocket. The unit is completely self-contained and is not connected to an extraneous energy source nor to outside instrumentation.

Referring now to FIGS. 1 through 4, an exemplified physical embodiment of the invention is shown in detail. The device consists of an elongated housing 18 having a first end 18A and a second end 18B. As shown in FIG.

4, in the illustrated arrangement the housing is rectangular, and more precisely, square in cross-sectional configuration, although the housing is not limited to such geometrical arrangement and may be of other cross-sectional shapes, such as circular.

The housing 18 includes a notch 20 intermediate the ends 18A and 18B, the notch extending only partially through the width of the housing and being dimensioned so as to freely receive the largest drip chamber to which the device is designed to be used.

As shown in the front view of FIG. 1, housing 18 includes a display window 22, typically closed with a transparent material and providing view of a liquid crystal display 24 which reveals during normal operating condition, the rate of the fluid flow such as in milliliters per hour. The display is also used to reveal drop size information and other indications as will be set forth hereinafter.

The housing 18 includes a fountain pen type clip 26 so that the user may clip the rate meter to a shirt or coat pocket The end 18B, as shown in FIG. 4, includes a slide out cover which serves as a means of replacing a battery 30 contained in the instrument.

Received on housing 18 is a slideable portion 32 which, as shown in FIG. 4, is of C-shaped cross-sectional configuration for ease in assembly onto the housing. One end 34 of slideable portion 32 has a semi-circular shape (best illustrated in FIGS. 2 and 3) which complements the opposed portion of notch 20. The primary function of the housing sliding portion 32 is to retain the rate meter in position on a drip chamber. An integral boss portion 36 extends within housing 18 and is engaged by a compression spring 38 so that the sliding portion 32 is urged in the direction towards housing end 18A. To secure the rate meter onto a drip chamber the housing portion 32 is slid in the direction towards housing end 18B, as shown in FIG. 3. The device is then positioned so that a drip chamber is received in notch 20. When manual force on the slidable portion 32 is released, spring 38 forces the moveable portion against the drip chamber, thereby holding the rate meter in position. To remove the instrument it is only necessary for the operator to hold the housing 18 and slide the moveable portion 32 to the right, that is, towards 18B.

The last remaining external feature of the rate meter to be described is a button switch 40, as seen in FIG. 1. This switch, as will be described in more detail subsequently, is used as one of its purposes, for setting the instrument to respond to the drop size of the equipment with which it is used.

The rate meter functions to measure flow rate of an IV administration system by detecting each drop of fluid as it falls downwardly through the drip chamber. This is accomplished by transmitting light beams across the drip path and detecting aberations in the light received as affected when drops pass through light beams. First and second light emitters 42 and 44 are positioned within the housing, on one side of notch 20. A photodetector 46 is positioned on the opposite side of notch 20 to receive the light beams 42A and 44A from the emitters.

The light emitters and photodetector are arranged in a horizontal plane. As shown in FIG. 6 (a diagrammatic arrangement of the light emitters and photodetectors), the light emitters are spaced apart from each other so that the beams 42A and 44A are at an angle A to each other. This arrangement gives a broader horizontal area for detecting the presence of a fluid drop as it passes through the drip chamber, as compared with a use of a single photo emitter. The use of two photo emitters has other advantages as will be set forth hereinafter.

In designing and implementing circuitry for the rate meter it is highly advantageous that the same amount of light be received by the photodetector 46 from each of the light emitters. This becomes a serious problem since only one light emitter can provide a beam which is directly in alignment with the photodetector optical axis. Since the other light emitter must be out of direct alignment the light transmitted by it is received by the photodetector at an angle relative to its axis of maximum optical sensitivity and therefore the effective quantity of light received by the photodetector from the second light emitter is reduced. The present invention provides a way so that the effective light intensity of both emitters is the same using the same energization power. The manner in which this is achieved is illustrated diagrammatically in FIG. 6. The spacing between the first light emitter 42 and photodetector 46 is $D_1$, with the light beam 42A being coincident the axis of maximum optical sensitivity of the photodetector. The second light emitter 44 transmits a beam 44A which is at an angle A from the axis of maximum sensitivity of the photodetector. By moving the second light emitter 44 closer to the photodetector 46, at a spacing $D_2$, the quantity of light from emitter 44 is equalized with that from first light emitter 42. It can be seen that as the angle A increases, the ratio of $D_2$ to $D_1$ decreases. By properly selecting $D_2$ for a selected angle A the same power applied to first and second light emitters 42 and 44 will produce the same voltage signal output on photodetector 46. Further by making $D_2$ sufficiently short as shown in FIG. 6, second light emitter 44 can be close to beam 42A since the light emitters do not physically interfere with each other. This arrangement enables the usage of the same circuit components for energizing both light emitters.

An important feature of the rate meter is that it does not employ an ON-OFF power switch. There are several reasons why it is desirable that the use of an ON-OFF switch be avoided First, a manual switch requires operation personnel to remember to turn the switch OFF when the instrument is not in use. The chance that the meter will be inadvertently left ON is significant, and therefore the average battery life can be expected to be relatively short. By eliminating the need for the operator to remember to turn On and OFF a power switch, the average useful life of the batteries is improved. Second, a power switch, when actuated, causes electronic signal bounce. In order to alleviate this problem it is usually necessary to incorporate a debouncing circuit. The need for a debouncing circuit is obviated by eliminating the ON-OFF switch A third reason is that any mechanical power switching device is subject to failure at a rate more rapidly than solid state electronic components.

In the rate meter of this invention a system is employed within the circuit and software to automatically ascertain when the device is not being used to measure a flow rate and therefore to turn it to the "OFF" mode, that is, the condition of minimal power consumption. One of the means for accomplishing this is by the use of a shutter, or occluder 48 which is a portion of the housing sliding portion 32. The occluder is seen in FIGS. 1, 2, 3 and 7. When the housing portion 32 is in the open position such as shown in FIG. 3, the occluder 48 is moved to the right so that light beam 44A is unobstructed. However, when the device is not mounted on a drip chamber and the slideable portion 32 is in the closed position as shown in FIGS. 1 and 2, the occluder 48 is moved into the path of light beam 44A, preventing it from impinging on the photo detector 46. In FIG. 7, the occluder 48 is shown in solid outline to indicate its position when the instrument is on a drip chamber and in dotted outline when it is not on a drip chamber.

Referring to FIGS. 7 and 8, the means wherein the occluder 48 functions to provide a power OFF signal is illustrated. FIG. 7 is a circuit diagram of the basic components of the rate meter. Mounted within housing 18 is a microcomputer 50, an analog signal conditioning circuit 52, a comparator 54, an oscillator 56 and a voltage reference circuit 58. Oscillator 56 provides a timing signal in the usual manner. The comparator 54 and voltage reference 58 are employed for determining the status of battery 30, that is, to ascertain that the battery 30 provides a sufficient voltage so that a reliable indication of flow rate is attainable A potentiometer 60 is employed during manufacture to set the threshold for the low battery comparator voltage.

FIG. 8 is a flow chart of the automatic OFF features of the rate meter The flow chart shows the sequence of the program for verifying that the battery voltage is at a preselected level as determined by comparator 54, that the occluder 48 is not obstructed light beam 44A, and that drops have been detected within a preselected maximum time duration.

In order to reduce maximum current drain on battery 30 the programmed instructions may be arranged to cause light emitters 42 and 44 to be pulsed one at a time.

Energy is conserved in the flow meter by powering many of the circuit elements, such as the optical detector 46, the light emitters 42 and 44, and analog conditioning circuit 52 directly from output lines from the microcomputer 50. The microcomputer removes power from the external circuit elements and enters a low power stop mode according to the following criteria (a) If the optical assembly is removed from the drip chamber, that is, occluder 48 intercepts light beam 44A; or (b) If the time before energizing the rate meter and placing the assembly on the drip chamber exceeds some nominal time, that is, approximately 15 seconds, which indicates that the rate meter was accidentally energized; or (c) If the rate meter is being used to monitor the IV flow rate and no drops are seen for approximately 50 seconds, the assumption being that the flow of IV fluid through the drip chamber has ceased; or (d) If the rate meter is being used to monitor the IV flow rate for longer than approximately 2½ minutes, the assumption being that the rate meter has been left unattended and need not operate; or (e) If a low battery condition is detected.

The flow chart of FIG. 9 illustrates the basic software arrangement for setting the drop size in drops per milliliter. Switch 40 is depressed, when the program is in the calibration mode, a number of times in order to increment to one of several pre-programmed drop sizes expressed as the number of drops to form a milliliter, which is established by the manufacturer of the IV equipment with which the rate meter is used. When switch 40 is first depressed while the rate meter was in the OFF mode, the last selected drop size is first displayed as a matter of convenience.

The software employed in the rate meter, as indicated partially and generally in the flow charts of FIGS. 8 and 9, is exemplary of microcomputer instructions for practicing the invention employing the basic circuit arrangement of FIG. 7 and the structural features of the invention as has been described. The method of detecting the presence of a drop as it passes through a drip chamber and alters the light impinging on optical detector 46 is a well known procedure as revealed in prior published material, such as in the prior issued patents listed in the summary of the invention.

The invention provides a unique rate meter for monitoring the flow rate of intravenous solutions. The rate meter is a small, compact, highly portable device which can be carried in the shirt or coat pocket of a user. It is expeditiously placed onto or removed from a drip chamber without requiring any tools. It is of light weight so as not to require supplemental support and so as not to cause portions of the IV fluid administration system to tend to separate from each other. The device includes means of reducing battery current consumption to prolong the life of the internally employed battery and at the same time in a manner which does not utilize an ON-OFF switch. The rate meter includes internal arrangements for monitoring its own status and for minimizing power consumption according to the status without requiring input from the user. In general, the rate meter has been herein described to provide a device having convenience and utility exceeding the present commercially practiced state of the art.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A rate meter for use on a transparent drip chamber of an IV fluid administration system comprising:

a housing adapted to be removeably affixed to a drip chamber whereby a first portion of the housing extends on one side of the drip chamber and a second portion of the housing extends on the opposite side of the drip chamber;

a photodetector in said housing first portion, the photodetector having an optical axis and characterized in that the voltage output therefrom is at a maximum in response to light received which is coincident with the optical axis and the voltage output therefrom is reduced in response to light received which is at an angle A to the optical axis, the voltage output being inversely related to angle A;

a first light emitter in said housing second portion providing, when energized, a light beam which is substantially coincident with said photodetector optical axis, and which is spaced a distance $D_1$ from said photodetector;

a second light emitter in said housing second portion providing, when energized, a light beam which is spaced a distance $D_2$ from said photo detector, and wherein $D_2$ is less than $D_1$ and wherein $D_1$, $D_2$ and A are selected so that the voltage output of the said photodetector is substantially the same when each of said light emitters is energized at equal power, the light beams of both light emitters being affected by drops of IV fluid; and means of displaying the rate of IV fluid flow in response to detected drops.

2. A rate meter according to claim 1 wherein said second housing portion is moveable relative to said first housing portion, the moveable portion being moved to open position to permit the attachment of the housing to a drip chamber, and to a closed position when the housing is not attached to a drip chamber, and including an occuluder means rigidly affixed to said housing moveable portion and arranged to intercept the light beam from one of said light emitters when said housing moveable portion is in the closed position.

3. A rate meter according to claim 2 including means responsive to the position of said occluder means to provide OFF or ON mode circuit conditions.

4. A rate meter according to claim 1 wherein said light emitters are pulsed one at a time to thereby reduce the maximum current drain on said battery.

5. A rate meter according to claim 1 including means wherein when the rate meter is not in use on a drip chamber an occluder intercepts the light from one of said light emitters to change the rate meter to an OFF mode during which current drain on said battery is minimized.

* * * * *